United States Patent [19]

Ushikubo et al.

[11] Patent Number: 5,750,760
[45] Date of Patent: May 12, 1998

[54] METHOD FOR PRODUCING A NITRILE

[75] Inventors: Takashi Ushikubo; Yukio Koyasu; Hiroya Nakamura, all of Yokohama, Japan

[73] Assignee: Mitsubishi Chemical Corporation, Tokyo, Japan

[21] Appl. No.: 717,194

[22] Filed: Sep. 20, 1996

[30] Foreign Application Priority Data

Oct. 5, 1995 [JP] Japan .................. 7-258607

[51] Int. Cl.$^6$ .................. C07C 253/26
[52] U.S. Cl. .................. 558/319
[58] Field of Search .................. 558/319

[56] References Cited

U.S. PATENT DOCUMENTS

| | | | |
|---|---|---|---|
| 4,746,641 | 5/1988 | Guttmann et al. | 502/202 |
| 4,784,979 | 11/1988 | Toft et al. | 502/8 |
| 4,788,317 | 11/1988 | Guttmann et al. | 558/319 |
| 4,879,264 | 11/1989 | Toft et al. | 502/8 |
| 5,049,692 | 9/1991 | Hatano et al. | 558/319 |
| 5,079,207 | 1/1992 | Brazdil et al. | 502/205 |
| 5,231,214 | 7/1993 | Ushikubo et al. | 558/319 |
| 5,281,745 | 1/1994 | Ushikubo et al. | 558/319 |
| 5,422,328 | 6/1995 | Ushikubo et al. | 502/312 |
| 5,472,925 | 12/1995 | Ushikubo et al. | 502/312 |
| 5,534,650 | 7/1996 | Ushikubo et al. | 558/319 |

FOREIGN PATENT DOCUMENTS

| | | |
|---|---|---|
| 0 082 620 | 6/1983 | European Pat. Off. . |
| 0 389 701 | 10/1990 | European Pat. Off. . |
| 0 512 846 | 11/1992 | European Pat. Off. . |
| 0 529 853 | 3/1993 | European Pat. Off. . |

Primary Examiner—Johann Richter
Assistant Examiner—Ebenezer Sackey
Attorney, Agent, or Firm—Oblon, Spivak, McClelland, Maier & Neustadt, P.C.

[57] ABSTRACT

A method for producing a nitrile, which comprises a gas phase catalytic oxidation reaction of an alkane with ammonia in the presence of an oxide catalyst of the empirical formula (1):

$$Mo_a V_b Sb_c X_x O_n \qquad (1)$$

wherein X is at least one element selected from the group consisting of Nb, Ta, W, Ti, Zr, Cr, Mn, Fe, Ru, Co, Rh, Ni, Pd, Pt, B, In, Ce, an alkali metal and an alkaline earth metal; when a=1, $0.1 \leq b < 0.99$, $0.01 \leq c < 0.9$, $0 \leq x < 0.89$, and $0.11 \leq (b+c+x) < 1$; and n is a number determined by the oxidized states of other elements.

9 Claims, No Drawings

METHOD FOR PRODUCING A NITRILE

The present invention relates to a method for producing a nitrile. Particularly, it relates to an improved method for producing a nitrile using an alkane as the starting material.

Nitriles such as acrylonitrile and methacrylonitrile have been industrially produced as important intermediates for the preparation of fibers, synthetic resins, synthetic rubbers and the like. Known as the most popular method for their production, is a method wherein an olefin such as propylene or isobutene is catalytically reacted with ammonia and oxygen at a high temperature in a gas phase in the presence of a catalyst.

On the other hand, in view of the price difference between propane and propylene or the price difference between isobutane and isobutene, an attention has recently been drawn to development of a method for producing acrylonitrile or methacrylonitrile by a so-called ammoxidation reaction method wherein a lower alkane such as propane or isobutane is used as the starting material, and such a lower alkane is catalytically reacted with ammonia and oxygen in a gas phase in the presence of a catalyst.

Such catalysts so far reported, are generally classified into those containing molybdenum (Mo) and those containing no molybdenum. As a catalyst containing no molybdenum as an essential component, a V—Sb—O catalyst (Japanese Unexamined Patent Publication No. 33783/1972, Japanese Examined Patent Publication No. 23016/1975, and Japanese Unexamined Patent Publications No. 268668/1989 and No. 180637/1990), a Sb—U—V—Ni—O catalyst (Japanese Examined Patent Publication No. 14371/1972), a Sb—Sn—O catalyst (Japanese Examined Patent Publication No. 28940/1975) or a V—Sb—W—P—O catalyst (Japanese Unexamined Patent Publication No. 95439/1990) has, for example, been reported.

On the other hand, as a system containing molybdenum, a Mo—Bi—P—O catalyst (Japanese Unexamined Patent Publication No. 16887/1973), a catalyst prepared by mechanically mixing a V—Sb—W—O oxide and a Bi—Ce—Mo—W—O oxide (Japanese Unexamined Patent Publication No. 38051/1989), a Ag—Bi—V—Mo—O catalyst (Japanese Unexamined Patent Publication No. 58961/1991), a Sn—V—Mo—Bi—O catalyst (Japanese Unexamined Patent Publication No. 247060/1992) or a Mo—V—Te—Nb—O catalyst (Japanese Unexamined Patent Publication No. 257/1990) has, for example, been known.

However, none of these conventional methods is sufficiently satisfactory in the yield of the intended nitriles. Further, it is common to require a quite high reaction temperature of about 500° C. or higher, such being disadvantageous from the viewpoint of the production cost and the material for the reactor. Further, in order to improve the yield of nitriles, a method of adding a small amount of an organic halide, an inorganic halide, a sulfur compound or water to the reaction system, has, for example, been attempted. However, the first three components bring about a problem of corrosion of the reaction apparatus, and water has a problem of formation of a by-product due to a side reaction and treatment thereof. Thus, each method has a difficulty in its industrial application.

To improve the yield of the desired nitrile without adding a halide, a sulfur compound or water to such a reaction system, there have been active developments of catalysts as mentioned above, and in recent years, there have been many reports on improvements, particularly with respect to an oxide catalyst system containing Mo, V and Te as the main components and an oxide catalyst system containing V and Sb as the main components.

However, the reaction results or the reaction conditions under which such catalysts are used, have not yet been fully satisfactory, or in some cases, vaporization of the catalyst-constituting elements is observed.

The present inventors have conducted extensive studies on various metal oxides as novel catalysts different from conventional reports, to be used in a method for producing a nitrile using an alkane as the starting material and as a result, have found that by a gas phase catalytic reaction of an alkane with ammonia in the presence of an oxide catalyst comprising molybdenum (Mo), vanadium (V) and antimony (Sb) as essential components, it is possible to produce a desired nitrile at a relatively low temperature of a level of from 340° to 480° C. in a yield higher than the conventional methods, without presence of a halide or water in the reaction system. The present invention has been accomplished on the basis of this discovery.

That is, the present invention provides a method for producing a nitrile, which comprises a gas phase catalytic oxidation reaction of an alkane with ammonia in the presence of an oxide catalyst of the empirical formula (1):

$$Mo_aV_bSb_cX_xO_n \qquad (1)$$

wherein X is at least one element selected from the group consisting of Nb, Ta, W, Ti, Zr, Cr, Mn, Fe, Ru, Co, Rh, Ni, Pd, Pt, B, In, Ce, an alkali metal and an alkaline earth metal; when a=1, $0.1 \leq b < 0.99$, $0.01 \leq c < 0.9$, $0 \leq x < 0.89$, and $0.11 \leq (b+c+x) < 1$; and n is a number determined by the oxidized states of other elements.

Now, the present invention will be described in detail with reference to the preferred embodiments.

In the composite oxide of the empirical formula (1) to be used in the present invention, X is at least one element selected from the group consisting of Nb, Ta, W, Ti, Zr, Cr, Mn, Fe, Ru, Co, Rh, Ni, Pd, Pt, B, In, Ce, an alkali metal and an alkaline earth metal, preferably at least one element selected from the group consisting of Nb, Ta, W, Ti, Fe and Ce, more preferably Nb, and/or Ce.

Further, a, b and c and x in the empirical formula (1) are preferably such that when a=1, $0.1 \leq b < 0.6$, $0.05 \leq c < 0.4$ and $0.01 \leq x \leq 0.6$. The ratio of c/b is not particularly limited, but it is usually at most 1, preferably at most 0.8, more preferably from 0.01 to 0.7.

In the present invention, firstly, a catalyst precursor having the same metal composition as the catalyst is prepared from an aqueous solution (in this specification, "an aqueous solution" includes not only a solution wherein a solute is completely dissolved but also a solution in a slurry state wherein a part of the solute is present undissolved).

The method for preparing an aqueous solution of the catalyst precursor having the same metal component as the catalyst, may, for example, be a method of adding and mixing a compound containing molybdenum (Mo) and a compound containing an element represented by X to an aqueous solution containing a vanadium (V) component and an antimony (Sb) component, to obtain an aqueous solution having the same metal composition as the desired catalyst, or a method of adding and mixing a compound containing vanadium (V) and a compound containing an element represented by X to an aqueous solution containing a molybdenum (Mo) component and an antimony (Sb) component, to obtain an aqueous solution having the same metal composition as the desired catalyst.

As the V material, a compound containing V, such as ammonium metavanadate, $V_2O_5$, $VOCl_3$ or $VO(OC_2H_5)_3$, may, for example, be mentioned. As the Mo material, a compound containing Mo, such as ammonium paramolybdate, $MoO_3$, $Mo(OC_2H_5)_5$, $MoCl_5$ or molybden-acetyl acetonate, may, for example, be mentioned. As the Sb material, $Sb_2O_3$, $Sb_2O_4$, SbOCl or $SbCl_3$ may, for example, be mentioned.

The compound containing an element represented by X, such as Nb, may, for example, be ammonium niobium oxalate, $Nb_2O_5$, $NbCl_5$ or $Nb(OC_2H_5)_5$, and the compound containing Ce may, for example, be $Ce(OH)_4$.

The method for producing the catalyst precursor by adding and mixing a compound containing Mo and a compound containing an element represented by X to an aqueous solution containing a V component and an Sb component to obtain an aqueous solution having the same metal composition as the desired catalyst, may, for example, be a method wherein as the V material, a solution containing an oxoanion containing pentavalent V is used, and as the Sb material, an antimony compound containing trivalent Sb is used, to obtain a catalyst precursor containing vanadium and antimony, wherein at least a part of V is reduced, and at least a part of Sb is oxidized to a pentavalent state. Likewise, the method for producing the catalyst precursor by adding and mixing a compound containing V and a compound containing an element represented by X to an aqueous solution containing a Mo component and an Sb component to obtain an aqueous solution having the same metal composition as the desired catalyst, may, for example, be a method wherein as the Mo material, a solution containing an oxoanion containing hexavalent Mo is used, and as the Sb material, an antimony compound containing trivalent Sb is used, to obtain a catalyst precursor containing molybdenum and antimony, wherein at least a part of Mo is reduced, and at least a part of Sb is oxidized to a pentavalent state.

Now, the method for producing the catalyst will be described with reference to the method of adding and mixing a compound containing Mo and a compound containing an element represented by X to an aqueous solution containing a V component and an Sb component to obtain an aqueous solution having the same metal composition as the desired catalyst.

The aqueous solution containing V and Sb may be a uniform solution or a slurry in a suspension state. Further, when the material is insoluble in water, an acid or alkali may be used for dissolving it, or the solution may be heated to a temperature of from 50° to 90° C. to facilitate the dissolution. The concentration of the aqueous solution is optional. However, the total amount of the compounds as starting materials is usually from 5 to 60 wt %, preferably from 10 to 30 wt %.

The compound containing Mo and the compound containing an element represented by X, to be added to the aqueous solution containing V and Sb, may be added in the form of their aqueous solutions or in the solid states as they are.

The aqueous solution having the same metal composition as the desired catalyst composition, thus prepared, is then dried by a method of evaporation to dryness, a spray drying method or a vacuum drying method, to obtain the catalyst precursor.

The catalyst precursor is then baked usually at a temperature of from 350° to 700° C., preferably from 400° to 700° C., usually for from 0.5 to 30 hours, preferably from 1 to 10 hours, to obtain the desired composite oxide. The baking may be conducted in an oxygen atmosphere, but is preferably conducted in the absence of oxygen. Specifically, it may be carried out in an inert gas atmosphere such as nitrogen, argon or helium, or in vacuum.

The composite oxide of the empirical formula (1) thus obtained, may be used by itself as a catalyst or may be used as supported on a well known carrier containing substantially no aluminum, such as silica, titania or diatomaceous earth. The catalyst may be formed into an appropriate shape and particle size depending upon the scale or system of the reaction.

Heretofore, as a carrier for a catalyst containing V and Sb as essential components, alumina or a metal oxide containing alumina has been preferably employed, since V, Sb and Al are considered to constitute a part of the catalytically active components. However, for the catalyst of the present invention, presence of Al in the catalyst is undesirable, and use of a catalyst carrier containing aluminum, such as alumina, is also undesirable, since the catalytic activities will be thereby impaired. This is believed attributable to the fact that the catalyst system of the present invention is different from the catalyst system comprising V and Sb, which has heretofore been reported, in the morphology of the active components effective for the reaction.

The method of the present invention is directed to the production of a nitrile by a gas phase catalytic oxidation reaction of an alkane with ammonia in the presence of the oxide catalyst of the empirical formula (1).

In the present invention, the alkane as the starting material is not particularly limited, and it may, for example, be methane, ethane, propane, butane, isobutane, pentane, hexane, heptane or cyclohexane. However, from the viewpoint of the industrial application of the obtainable nitrites, it is preferred to employ a lower alkane having from 3 to 8 carbon atoms, particularly propane or isobutane.

In the present invention, the composition of the feed gas is not particularly limited. However, the molar ratio of ammonia/alkane is usually from 0.1 to 5, preferably from 0.4 to 3, more preferably from 0.8 to 1.5, and the molar ratio of oxygen/alkane is usually from 0.1 to 10, preferably from 1.0 to 5, more preferably from 1.5 to 5.

The molecular oxygen in the feed gas may be pure oxygen gas. However, purity is not particularly required, and it is usually economical to use an oxygen-containing gas such as air.

Further, the gas space velocity SV in the gas phase catalytic oxidation reaction is usually within a range of from 100 to 10,000 $hr^{-1}$, preferably from 300 to 2,000 $hr^{-1}$. As a diluting gas to adjust the space velocity and the oxygen partial pressure, an inert gas such as nitrogen, argon or helium, may be employed. The reaction is carried out usually under atmospheric pressure, but it may be carried out under a low degree of pressure or under reduced pressure. The reactor system of the present invention may either be a fixed bed system or a fluidized bed system. However, for example, an ammoxidation reaction of propane is an exothermic reaction, whereby a fluidized bed system is preferred so that the reaction temperature can more easily be controlled.

According to the method of the present invention, by employing the oxide catalyst of the empirical formula (1), the ammoxidation reaction of an alkane can be carried out at a temperature lower than heretofore, i.e. usually at a level of from 340° to 480° C., preferably from 380° to 470° C.

The mechanism of the oxidation reaction in the present invention is not clearly understood, but it is believed that the oxidation reaction is carried out by oxygen atoms present in the oxide of the empirical formula (1) or by molecular oxygen present in the feed gas.

Now, the present invention will be described in further detail with reference to Examples. However, it should be understood that the present invention is by no means restricted to such specific Examples.

Further, the conversion (%), the selectivity (%) and the yield (%) in the following Examples, are represented by the following formulas, respectively.

Conversion of alkane (%)=(mols of consumed alkane/mols of supplied alkane)×100

Selectivity for desired nitrile (%)=(mols of formed desired nitrile/mols of consumed alkane)×100 Yield of desired nitrile (%)=(mols of formed desired nitrile/mols of supplied alkane)×100

EXAMPLE 1

A composite oxide having an empirical formula $Mo_1V_{0.3}Sb_{0.2}Nb_{0.05}O_n$ was prepared as follows.

In 325 ml of warm water, 15.7 g of ammonium metavanadate ($NH_4VO_3$) was dissolved, and 13.0 g of antimony trioxide ($Sb_2O_3$) powder was added thereto, whereupon the slurry was heated and aged for 6 hours, and then 78.9 g of ammonium paramolybdate (($NH_4)_6Mo_7O_{24}.4H_2O$) was added thereto to obtain a uniform slurry. Then, 10.0 g of an aqueous ammonium niobium oxalate solution having a Nb concentration of 2.23 mol/kg, was added thereto to obtain a slurry. This slurry was heat-treated to remove water and to obtain a solid. This solid was heated at 400° C. in air for salt decomposition, then molded into tablets of 5 mm in diameter×3 mm in length by means of a tabletting machine, then pulverized, sieved to from 16 to 28 mesh and then baked at 600° C. for 2 hours in a nitrogen stream.

0.55 g of a catalyst thus obtained was packed into a reactor, and a gas phase catalytic reaction was carried out at a reaction temperature of 410° C. at a space velocity SV of 549 hr$^{-1}$ by supplying a gas in a molar ratio of propane:ammonia:air=1:1.2:15. The results are shown in Table 1.

EXAMPLE 2

A composite oxide having an empirical formula $Mo_1V_{0.3}Sb_{0.3}Nb_{0.1}O_n$ was prepared in the same manner as in Example 1 except that in Example 1, the amount of the antimony trioxide ($Sb_2O_3$) powder was changed to 19.5 g, the amount of the aqueous ammonium niobium oxalate solution was changed to 20.0 g, and the baking temperature in the nitrogen stream was changed to 550° C.

0.55 g of the catalyst thus obtained was packed into a reactor, and a gas phase catalytic reaction was carried out at a reaction temperature of 430° C. at a space velocity SV of 1035 hr$^{-1}$ by supplying a gas in a molar ratio of propane:ammonia:air=1:1.2:15. The results are shown in Table 1.

EXAMPLE 3

A composite oxide having an empirical formula $Mo_1V_{0.3}Sb_{0.3}Nb_{0.05}O_n$ was prepared in the same manner as in Example 1 except that in Example 1, the amount of the antimony trioxide ($Sb_2O_3$) powder was changed to 19.5 g, and the baking temperature in the nitrogen stream was changed to 550° C.

0.55 g of the catalyst thus obtained was packed into a reactor, and a gas phase catalytic reaction was carried out at a reaction temperature of 410° C. at a space velocity SV of 823 hr$^{-1}$ by supplying a gas in a molar ration of propane:ammonia:air=1:1.2:15. The results are shown in Table 1.

EXAMPLE 4

A composite oxide having an empirical formula $Mo_1V_{0.3}Sb_{0.3}O_n$ was prepared in the same manner as in Example 1 except that in Example 1, the amount of the antimony trioxide ($Sb_2O_3$) powder was changed to 19.5 g, no ammonium niobium oxalate was added, and the baking temperature in the nitrogen stream was changed to 550° C.

0.55 g of the catalyst thus obtained was packed into a reactor, and a gas phase catalytic reaction was carried out at a reaction temperature of 430° C. at a space velocity SV of 680 hr$^{-1}$ by supplying a gas in a molar ratio of propane:ammonia:air=1:1.2:15. The results are shown in Table 1.

EXAMPLE 5

A composite oxide having an empirical formula $Mo_1V_{0.3}Sb_{0.3}Nb_{0.05}O_n$ was prepared as follows.

In 325 ml of warm water, 78.9 g of ammonium paramolybdate (($NH_4)_6Mo_7O_{24}.4H_2O$) was dissolved, and 19.5 g of antimony trioxide ($Sb_2O_3$) powder was added thereto, whereupon the slurry was heated and aged for 6 hours, and then 15.7 g of ammonium metavanadate ($NH_4VO_3$) was added thereto to obtain a uniform slurry. Then, 10.0 g of an aqueous ammonium niobium oxalate solution having a Nb concentration of 2.23 mol/kg was added thereto to obtain a slurry. This slurry was heat-treated to remove water and to obtain a solid. This solid was heated at 400° C. in air for salt decomposition, then molded into tablets of 5 mm in diameter×3 mm in length by means of a tabletting machine, then pulverized, sieved to from 16 to 28 mesh and baked at 550° C. for 2 hours in a nitrogen stream.

0.55 g of the catalyst thus obtained was packed into a reactor, and a gas phase catalytic reaction was carried out at a reaction temperature of 410° C. at a space velocity SV of 517 hr$^{-1}$ by supplying a gas in a molar ratio of propane:ammonia:air=1:1.2:15. The results are shown in Table 1.

EXAMPLE 6

A composite oxide having an empirical formula $Mo_1V_{0.3}Sb_{0.15}Nb_{0.05}O_n$ was prepared in the same manner as in Example 1 except that in Example 1, the amount of the antimony trioxide ($Sb_2O_3$) powder was changed to 9.8 g, the amount of the aqueous ammonium niobium oxalate solution was changed to 10.0 g, and the baking temperature in the nitrogen stream was changed to 600° C.

0.55 g of the catalyst thus obtained was packed into a reactor, and a gas phase catalytic reaction was carried out at a reaction temperature of 410° C. at a space velocity SV of 522 hr$^{-1}$ by supplying a gas in a molar ratio of propane:ammonia:air=1:1.2:15. The results are shown in Table 1.

EXAMPLE 7

A composite oxide having an empirical formula $Mo_1V_{0.3}Sb_{0.16}Nb_{0.05}O_n$ was prepared in the same manner as in Example 1 except that in Example 1, the amount of the antimony trioxide ($Sb_2O_3$) powder was changed to 10.4 g, the slurry was cooled immediately after the addition of ammonium paramolybdate, the slurry was cooled to 15° C. or lower at the time of adding ammonium niobium oxalate, the salt decomposition temperature in air was changed to 380° C., and the baking temperature in a nitrogen stream was changed to 615° C.

0.55 g of the catalyst thus obtained was packed into a reactor, and a gas phase catalytic reaction was carried out at a reaction temperature of 420° C. at a space velocity SV of 440 hr$^{-1}$ by supplying a gas in a molar ration of propane:ammonia:air=1:1.2:15. The results are shown in Table 1.

EXAMPLE 8

A composite oxide having an empirical formula $Mo_1V_{0.3}Sb_{0.15}Nb_{0.05}Ce_{0.01}O_n$ was prepared in the same manner as in Example 1 except that in Example 1, the amount of the antimony trioxide ($Sb_2O_3$) powder was changed to 9.75 g, the slurry was cooled immediately after the addition of ammonium paramolybdate, the slurry was cooled to 15° C. or lower at the time of adding ammonium niobium oxalate, 0.93 g of cerium hydroxide $Ce(OH)_4$ was added after the addition of ammonium niobium oxalate, the salt decomposition temperature in air was changed to 380° C., and the baking temperature in the nitrogen stream was changed to 610° C.

0.55 g of the catalyst thus obtained was packed into a reactor, and a gas phase catalytic reaction carried out at a reaction temperature of 430° C. at a space velocity SV of 490 hr$^{-1}$ by supplying a gas in a molar ration of propane:ammonia:air=1:1.2:15. The results are shown in Table 1.

EXAMPLE 9

A composite oxide having an empirical formula $Mo_1V_{0.3}Sb_{0.15}Nb_{0.05}Ce_{0.02}O_n$ was prepared in the same manner as in Example 1 except that in Example 1, the amount of the antimony trioxide ($Sb_2O_3$) powder was changed to 9.75 g, the slurry was cooled immediately after the addition of ammonium paramolybdate, the temperature of the slurry at the time of addition of ammonium niobium oxalate was maintained at a level of at most 15° C., 1.86 g of cerium hydroxide $Ce(OH)_4$ was added after the addition of ammonium niobium oxalate, the salt decomposition temperature in air was changed to 380° C., and the baking temperature in the nitrogen stream was changed to 620° C.

0.55 g of the catalyst thus obtained was packed into a reactor, and a gas phase catalytic reaction was carried out at a reaction temperature of 430° C. at a space velocity SV of 600 hr$^{-1}$ by supplying a gas in a molar ratio of propane:ammonia:air=1:1.2:15. The results are shown in Table 1.

EXAMPLE 10

A composite oxide having an empirical formula $Mo_1V_{0.3}Sb_{0.15}Nb_{0.05}Ce_{0.03}O_n$ was prepared in the same manner as in Example 1 except that in Example 1, the amount of the antimony trioxide ($Sb_2O_3$) powder was changed to 9.75 g, the slurry was cooled immediately after the addition of ammonium paramolybdate, the temperature of the slurry at the time of adding ammonium niobium oxalate was maintained at most 15° C., 2.78 g of cerium hydroxide $Ce(OH)_4$ was added after the addition of ammonium niobium oxalate, the salt decomposition temperature in air was changed to 380° C., and the baking temperature in the nitrogen stream was changed to 610° C.

0.55 g of the catalyst thus obtained was packed into a reactor, and a gas phase catalytic reaction was carried out at a reaction temperature of 430° C. at a space velocity SV of 490 hr$^{-1}$ by supplying a gas in a molar ration of propane:ammonia:air=1:1.2:15. The results are shown in Table 1.

EXAMPLE 11

A composite oxide having an empirical formula $Mo_1V_{0.3}Sb_{0.15}Nb_{0.05}Ce_{0.02}O_n$ was prepared in the same manner as in Example 1 except that in Example 1, the amount of the antimony trioxide ($Sb_2O_3$) powder was changed to 9.75 g, the slurry was cooled before the addition of ammonium paramolybdate, the temperature of the slurry at the time of adding ammonium niobium oxalate was maintained at most 30° C., 1.86 g of cerium hydroxide $Ce(OH)_4$ was added after the addition of ammonium niobium oxalate, the salt decomposition temperature in air was changed to 380° C., and the baking temperature in a nitrogen stream was changed to 620° C.

0.55 g of the catalyst thus obtained was packed into a reactor, and a gas phase catalytic reaction was carried out at a reaction temperature of 430° C. at a space velocity SV of 610 hr$^{-1}$ by supplying a gas in a molar ration of propane:ammonia:air=1:1.2:15. The results are shown in Table 1.

COMPARATIVE EXAMPLE 1

A composite oxide having an empirical formula $Mo_1V_{0.3}Sb_{0.2}Nb_{0.05}Al_1O_n$ was prepared as follows.

In 325 ml of warm water, 15.7 g of ammonium metavanadate ($NH_4VO_3$) was dissolved, and 13.0 g of antimony trioxide ($Sb_2O_3$) powder was added thereto, whereupon the slurry was heated and aged for 6 hours, and then 78.9 g of ammonium paramolybdate (($NH_4)_6Mo_7O_{24}\cdot 4H_2O$) was added thereto to obtain a uniform slurry. Then, 10.0 g of an aqueous ammonium niobium oxalate solution having a Nb concentration of 2.23 mol/kg and 272.2 g of alumina sol having an Al concentration of 1.67 mol/kg, were sequentially added thereto to obtain a slurry. This slurry was heat-treated to remove water and to obtain a solid. This solid was heated at 400° C. in air for salt decomposition, then molded into tablets of 5 mm in diameter×3 mm in length by means of a tabletting machine, then pulverized, sieved to from 16 to 28 mesh and then baked at 600° C. for 2 hours in a nitrogen stream.

0.70 g of the catalyst thus obtained was packed into a reactor, and a gas phase catalytic reaction was carried out at a reaction temperature of 430° C. at a space velocity SV of 793 hr$^{-1}$ by supplying a gas in a molar ration of propane:ammonia:air=1:1.2:15. The result are shown in Table 1.

TABLE 1

| | Reaction temp. (°C.) | Space velocity SV (hr$^{-1}$) | Conversion of propane (%) | Selectivity for acrylonitrile (%) | Yield of acrylonitrile (%) |
|---|---|---|---|---|---|
| Example 1 | 410 | 549 | 86.7 | 53.2 | 46.2 |
| Example 2 | 430 | 1035 | 61.9 | 46.7 | 28.9 |
| Example 3 | 410 | 823 | 72.6 | 50.4 | 36.6 |
| Example 4 | 430 | 680 | 82.7 | 41.8 | 34.6 |
| Example 5 | 410 | 517 | 62.6 | 50.9 | 31.9 |
| Example 6 | 410 | 522 | 90.2 | 50.0 | 45.1 |
| Example 7 | 420 | 440 | 90.9 | 51.4 | 46.7 |
| Example 8 | 430 | 490 | 94.5 | 53.0 | 50.1 |
| Example 9 | 430 | 600 | 86.9 | 58.6 | 50.9 |
| Example 10 | 430 | 490 | 89.3 | 57.1 | 51.0 |
| Example 11 | 430 | 610 | 91.5 | 55.7 | 51.0 |
| Comparative Example 1 | 430 | 793 | 17.9 | 31.7 | 5.7 |

EXAMPLE 12

Using the same types and the same amounts of molybdenum, vanadium and antimony compounds and the same amount of water as used in Example 3, a composite oxide having an empirical formula $Mo_1V_{0.3}Sb_{0.2}Nb_{0.05}Fe_{0.06}O_n$ was prepared in the same manner as in Example 3 except that a predetermined amount of iron hydroxide Fe(OH)$_3$ was added at the time of heating and aging the slurry comprising ammonium metavanadate and antimony trioxide.

0.55 g of the catalyst thus obtained was packed into a reactor, and a gas phase catalytic reaction was carried out at a reaction temperature of 410° C. at a space velocity SV of 549 hr$^{-1}$ by supplying a gas in a molar ratio of propane:ammonia:air=1:1.2:15. As a result, the conversion of propane was 79.1%, the selectivity for acrylonitrile was 53.0%, and the yield of acrylonitrile was 43.1%.

COMPARATIVE EXAMPLE 2

A composite oxide having an empirical formula $Mo_1V_{0.3}Bi_{0.2}Nb_{0.05}O_n$ was prepared in the same manner as in Example 1 except that bismuth trioxide (Bi$_2$O$_3$) was used in stead of antimony trioxide in Example 1. Using the catalyst thus obtained, a gas phase catalytic reaction was carried out under the same reaction conditions as in Example 1. As a result, the conversion of propane was 10.6%, the selectivity for acrylonitrile was 16.5%, and the yield of acrylonitrile was 1.7%.

According to the method of the present invention, it is possible to produce a desired nitrile from an alkane at a relatively low reaction temperature in good yield even without presence of a halide or water in the reaction system.

What is claimed is:

1. A method for producing a nitrile, which comprises a gas phase catalytic oxidation reaction of an alkane with ammonia in the presence of an oxide catalyst of the empirical formula (1):

$$Mo_aV_bSb_cX_xO_n \quad (1)$$

wherein X is at least one element selected from the group consisting of Nb, Ta, W, Ti, Zr, Cr, Mn, Fe, Ru, Co, Rh, Ni, Pd, Pt, B, In, Ce, an alkali metal and an alkaline earth metal; when a=1, 0.1≦b<0.99, 0.01≦c<0.9, 0≦x<0.89, and 0.11≦(b+c+x)<1; and n is a number determined by the oxidized states of other elements.

2. The method according to claim 1, wherein the oxide catalyst of the empirical formula (1) is prepared by baking a catalyst precursor which is obtained by adding and mixing a compound containing molybdenum and a compound containing an element represented by X to an aqueous solution containing a vanadium component and an antimony component, followed by drying the aqueous solution.

3. The method according to claim 1, wherein the oxide catalyst of the empirical formula (1) is prepared by baking a catalyst precursor which is obtained by adding and mixing a compound containing vanadium and a compound containing an element represented by X to an aqueous solution containing a molybdenum component and an antimony component.

4. The method according to claim 1, wherein X in the empirical formula (1) is at least one element selected from the group consisting of Nb, Ta, W, Ti, Fe and Ce.

5. The method according to claim 1, wherein in the empirical formula (1), when a=1, 0.1≦b≦0.6, 0.05≦c<0.4, and 0.01≦x≦0.6.

6. The method according to claim 1, wherein in the empirical formula (1), b/c is at most 1.

7. The method according to claim 1, wherein the oxide catalyst of the empirical formula (1) is used for the gas phase catalytic oxidation reaction of an alkane, as supported on a carrier containing substantially no aluminum.

8. The method according to claim 1, wherein the alkane is propane or isobutane.

9. The method according to claim 1, wherein the reaction temperature of the gas phase catalytic oxidation reaction is from 340° to 480° C.